(12) United States Patent
Wang et al.

(10) Patent No.: US 7,737,179 B2
(45) Date of Patent: Jun. 15, 2010

(54) METHODS FOR TREATMENT OF DERMATOLOGICAL CONDITIONS

(75) Inventors: Bing Wang, Cupertino, CA (US); Sekhar Bodupalli, San Jose, CA (US); Xiangfeng Li, Cupertino, CA (US); Khalid Mahmood, Batavia, CA (US); Wei Zhang, Santa Clara, CA (US); Guy Miller, San Jose, CA (US)

(73) Assignee: J&J Consumer Companies, Inc., Skillman, NJ (US)

( * ) Notice: Subject to any disclaimer, the term of this patent is extended or adjusted under 35 U.S.C. 154(b) by 1055 days.

(21) Appl. No.: 10/910,095

(22) Filed: Aug. 2, 2004

(65) Prior Publication Data
US 2005/0032751 A1 Feb. 10, 2005

Related U.S. Application Data

(60) Provisional application No. 60/492,591, filed on Aug. 4, 2003, provisional application No. 60/542,934, filed on Feb. 9, 2004.

(51) Int. Cl.
*A01N 37/44* (2006.01)
(52) U.S. Cl. .................... 514/561; 514/553; 514/574
(58) Field of Classification Search ............... None
See application file for complete search history.

(56) References Cited

U.S. PATENT DOCUMENTS

| | | | |
|---|---|---|---|
| 2,421,707 A | 6/1947 | Malkemus | |
| 3,080,410 A | 3/1963 | LeBlanc | |
| 5,135,913 A | 8/1992 | Pickart | |
| 5,348,943 A | 9/1994 | Pickart | |
| 5,554,647 A | 9/1996 | Perricone | |
| 5,759,555 A | 6/1998 | Moy | |
| 5,928,659 A | 7/1999 | Moy | |
| 6,165,484 A | 12/2000 | Raad | |
| 6,235,773 B1 * | 5/2001 | Bissett | ............... 514/456 |
| 6,267,979 B1 | 7/2001 | Raad | |
| 6,471,972 B1 | 10/2002 | Bonte | |
| 6,544,531 B1 | 4/2003 | Cole | |
| 6,607,735 B2 | 8/2003 | Cole | |
| 6,743,433 B2 | 6/2004 | Perricone | |
| 2002/0049190 A1 | 4/2002 | Bridger et al. | |
| 2003/0026280 A1 | 2/2003 | De Lacharriere et al. | |
| 2003/0202951 A1 | 10/2003 | Cole | |
| 2003/0224028 A1 | 12/2003 | Galey | |
| 2004/0034042 A1 * | 2/2004 | Tsuji et al. | ............ 514/263.31 |
| 2004/0052826 A1 | 3/2004 | Fernandez-Kleinlein | |
| 2004/0081634 A1 | 4/2004 | Perricone | |

FOREIGN PATENT DOCUMENTS

| | | |
|---|---|---|
| DE | 2416556 | 10/1975 |
| DE | 2533101 | 2/1977 |
| EP | 89136 A2 | 9/1983 |
| JP | 7033720 A | 3/1995 |
| JP | 11-240886 | 9/1999 |
| RO | 108529 | 6/1994 |
| RO | 108530 | 6/1994 |
| WO | WO 99/09997 A | 3/1999 |
| WO | WO 03/088914 | 10/2003 |

OTHER PUBLICATIONS

The Merck Manuals, Online Medical Library, "Basal Cell Carcinoma", http://www.merck.com/mmhe/sec18/ch216/ch216b.html, revised Feb. 2003.*
The Merck Manuals, Online Medical Library, "Melanoma", http://www.merck.com/mmhe/sec18/ch216/216d.html, revised Feb. 2003.*
Vippagunta et al, Advanced Drug Delivery Reviews, 48, pp. 3-26 (2001).*
Database WPI Week 199515; Thomson Scientific, London, GB; AN 1995-110596 XP002492509.

* cited by examiner

*Primary Examiner*—Sharmila Gollamudi Landau
*Assistant Examiner*—Barbara Frazier

(57) ABSTRACT

A method of reducing the appearance of skin conditions associated with loss of skin tightness, skin firmness, or dark circles under the eyes with topical compositions comprising compounds of any of the Formulae I or Ia as described herein, is disclosed.

4 Claims, No Drawings

METHODS FOR TREATMENT OF DERMATOLOGICAL CONDITIONS

CROSS-REFERENCE TO RELATED APPLICATIONS

This application claims priority under 35 U.S.C. 119(e) to co-pending provisional applications U.S. Ser. No. 60/492,591 filed on Aug. 4, 2003, and U.S. Ser. No. 60/542,934 filed on Feb. 9, 2004, incorporated herein by reference in their entirety.

BACKGROUND INFORMATION

Skin wrinkles and sagging of tissue are undesired reminders of advanced age to many people in our youth-conscious society. Skin problems in individuals can result from a variety of extrinsic or intrinsic factors such as harmful UV radiation from the sun, exposure to the environment, stress, fatigue, disease, aging, or a combination thereof. With age the epidermis thins, sebaceous secretions decrease, the skin becomes more susceptible to dryness, chapping, and fissuring, and the dermis diminishes with loss of elastic and collagen fibers. This results in wrinkling and other forms of roughness, including but not limited to, increased pore size, flaking, mottling, discoloration, wrinkling, and skin lines.

In addition to changes on the surface of the skin, aging muscles lengthen due to the effects of gravity and to a loss of muscle tone. The combination of sagging muscles and aging skin contributes to the overall cosmetic changes typically observed with age, such as wrinkling which involves the transition of a formerly smooth skin surface to one that appears unevenly shrunk, lined, and contracted. Present treatments of placid skin and muscles range from cosmetic creams, moisturizers, acid peels and dermabrasion to various forms of cosmetic or plastic surgery.

A large number of skin care compositions are known in the art and used to improve the health and/or physical appearance of skin. Romanian patents RO 108,529, RO 108,530 and RO 108,642 describe the use of a day cream for the use on different types of skin comprising 0.001-0.1% diethylaminoethanol. Some monosubstituted dialkanolpiperazines have been claimed as emulsifying agents in the cosmetic industry in U.S. Pat. No. 2,421,707. German patent applications DE 2,533,101 and DE 2,416,556 disclose the use of alkanolamines as moisturizers. U.S. Pat. No. 5,554,647 to Perricone discloses that aging skin and muscles can be treated by the topical application of a precursor of the neurotransmitter acetylcholine, such as dimethylaminoethanol, monomethylaminoethanol, choline, or serine and mixtures thereof, as well as diethylaminoethanol, monoethylamino-ethanol, dipropylaminoethanol, monopropylaminoethanol, dibutylaminoethanol, and monobutylaminoethanol. U.S. Pat. No. 6,607,735 and US 2003/020951 relate to compositions containing dimethylaminoethanol (DMAE) and tyrosine to reduce puffiness of the skin under the eyes and the appearance of dark circles around the eyes. These compounds have unpleasant odor characteristics that prevent them of being optimal for the use in cosmetics, particularly for cosmetics applied to the human face. U.S. Pat. No. 5,135,913 and U.S. Pat. No. 5,348,943 relates to cosmetic compositions in general, and more specifically, to the use of derivatives of glycyl-L-histidyl-L-lysine: copper(II) (GHL—Cu) within skin treatment and cosmetic compositions.

While various agents have heretofore been provided for dermatological conditions, it has however been found that compounds of the present invention are odorless and provide superior benefits in reducing the appearance of skin imperfections and in their use as cosmetics.

SUMMARY OF THE INVENTION

The present invention relates to methods for reducing the appearance of visible and/or tactile discontinuities in skin associated with aging, age-related damage, or damage resulting from harmful UV radiation, pollution and other environmental insults, stress, or fatigue. The present invention also relates to methods for reducing the appearance of puffiness of skin under the eyes and the appearance of dark circles around and under the eyes. The invention concerns compositions and methods of improving skin appearance by lifting and firming the skin. The present invention excludes methods using compositions comprising aminoalkanols that are not precursors of the neurotransmitter acetylcholine such as dimethylaminoethanol (DMAE), for reducing the appearance of skin conditions on faces and neck that have developed prominent lines such as nasolabial folds, hanging of tissue from the mandibular region, and increased sagging of tissue around the eyes and other areas The present invention is concerned with the treatment of skin comprising topically applying to affected skin areas a composition comprising at least one compound represented by a general formula selected from the groups (i), (ii), (iii) and (iv):

i)

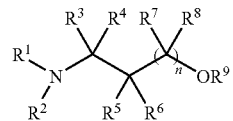

Formula I wherein
  n is 0, 1, or 2;
  $R^1$ is hydrogen, $C_1$-$C_6$-alkyl, $C_2$-$C_{12}$-alkenyl, hydroxyalkyl, carboxyalkyl, alkoxycarbonylalkyl, acetoxyalkyl, aminoalkyl, aminocarbonylalkyl, aryl, arylalkyl, heteroaryl, or heteroarylalkyl;
  $R^2$ is $C_1$-$C_6$-alkyl, $C_2$-$C_{12}$-alkenyl, carboxyalkyl, alkoxycarbonylalkyl, aminoalkyl, acetoxyalkyl, aminocarbonylalkyl, aryl, arylalkyl, heteroaryl, or heteroarylalkyl;
  $R^3$, $R^4$, $R^5$, $R^6$, $R^7$, or $R^8$ are independently of each other hydrogen, $C_1$-$C_6$-alkyl, hydroxyalkyl, or aminoalkyl; and
  $R^9$ is hydrogen, $C_1$-$C_6$-alkyl, phosphoryl, aryl, or acyl;
with the proviso that if $R^1$ is hydrogen, $C_1$-$C_3$-alkyl, or $C_2$-$C_4$ alkanol optionally bearing at least one carboxyl group and $R^2$ is $C_1$-$C_3$-alkyl; then —C($R^3R^4$)—C($R^5R^6$)—(C($R^7R^8$))$_n$—OR$^9$ is not $C_2$-$C_4$-alkanol optionally bearing at least one carboxyl group;

or ii)

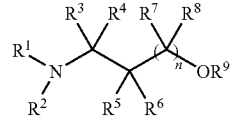

Formula I wherein
n, $R^1$ and $R^9$ are as defined above in group (i); and
$R^2$ and $R^3$, $R^2$ and $R^5$, and $R^5$, $R^2$ and $R^7$, or $R^2$ and $R^9$ together with the atom or atoms to which they are attached may form a 3- to 7-membered ring optionally incorporating one or more additional NR', O or S groups, wherein R' is $C_1$-$C_6$-alkyl, hydroxyalkyl, phenyl or phenylalkyl wherein the phenyl group is optionally substituted with one or more groups selected from hydroxy, alkyl, halogen, haloalkyl, carboxy, amino and nitro; and wherein the carbon atoms of said 3-to 7-membered ring may be further substituted with at least one $C_1$-$C_6$-alkyl, oxo, hydroxy, or hydroxyalkyl; and the $R^2$, $R^3$, $R^4$, $R^5$, $R^6$, $R^7$, or $R^8$ groups not forming a ring are independently of each other as defined above in group (i);

or
iii)

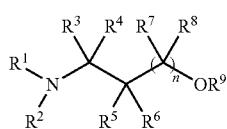

Formula I wherein
n, $R^3$, $R^4$, $R^6$, $R^7$, $R^8$ and $R^9$ are as defined above in group (i); and
$R^1$, $R^2$, and $R^5$ together with the atoms to which they are attached form a bicyclic ring;

or
iv)

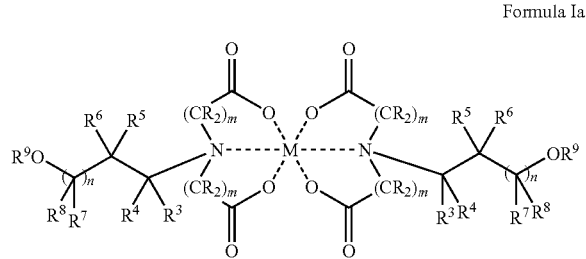

Formula Ia wherein
M is a metal;
m is 1, 2, 3, or 4;
R is independently hydrogen or $C_{1-6}$-alkyl, and n, $R^3$, $R^4$, $R^5$, $R^6$, $R^7$, $R^8$, or $R^9$ are as defined above in group (i);

or individual isomers, racemic or non-racemic mixtures of isomers, or acceptable salts or solvates thereof.

It is to be understood that when n is O, $CR^7R^8$ is not present and the group $OR^9$ is attached to the previous carbon, particularly to $CR^5R^6$.

It will be further understood by those skilled in the art with respect to any group containing one or more substituents that such groups are not intended to introduce any substitution or substitution patterns that are sterically impractical and/or synthetically non-feasible.

In one embodiment, the composition comprises a compound of Formula I wherein $R^1$ is hydrogen, $C_1$-$C_6$-alkyl, $C_2$-$C_{12}$-alkenyl, hydroxyalkyl, carboxyalkyl, alkoxycarbonylalkyl, phenyl, or benzyl, and $R^2$ is $C_1$-$C_6$-alkyl, $C_2$-$C_{12}$-alkenyl; hydroxyalkyl, diakylaminoalkoxyalkyl, carboxylalkyl, alkoxycarbonylalkyl, phenyl, or benzyl, wherein the phenyl or benzyl groups of $R^1$ or $R^2$ may be optionally substituted with hydroxy, cyano, nitro, halo, haloalkyl, thioalkyl, optionally substituted phenylvinyl, aminosulfonyl, sulfonylamino, carboxy, or alkoxycarbonyl.

In another embodiment, the composition comprises a compound of Formula I wherein $R^2$ and $R^3$ together with the atom to which they are attached form a 3- to 7-membered ring optionally incorporating —NR'—, —O— or —S— groups, wherein R' is $C_1$-$C_6$-alkyl, phenyl, or benzyl; wherein the phenyl group can be optionally substituted with hydroxy, cyano, nitro, halo, thioalkyl, optionally substituted phenylvinyl, aminosulfonyl, sulfonylamino, carboxy, or alkoxycarbonyl; and wherein said 3- to 7-membered ring may be further substituted; particularly wherein $R^2$ and $R^3$ together with the atom to which they are attached form a piperidine or a pyrrolidine ring, optionally substituted with $C_1$-$C_6$-alkyl or oxo.

In another embodiment, the composition comprises a compound of Formula I wherein $R^2$ and $R^5$ together with the atom to which they are attached form a 3- to 7-membered ring optionally incorporating —NR'—, —O— or —S— groups, wherein R' is $C_1$-$C_6$-alkyl, phenyl or benzyl; wherein the phenyl group can be optionally substituted with hydroxy, cyano, nitro, halo, thioalkyl, optionally substituted phenylvinyl, aminosultonyl, sulfonylamino, carboxy, or alkoxycarbonyl; and wherein said 3- to 7-membered ring may be further substituted with $C_1$-$C_6$-alkyl; particularly $R^2$ and $R^5$ together with the atom to which they are attached form a piperidine or a pyrrolidine ring, optionally substituted with $C_1$-$C_6$-alkyl or oxo.

In another embodiment, the composition comprises a compound of Formula I wherein $R^2$ and $R^9$ together with the atom to which they are attached form a 6- to 7-membered ring further substituted with an oxo group, preferably $R^2$ and $R^9$ together with the atom to which they are attached form a 2-oxo-morpholine ring, and R' is a carboxyalkyl.

In another embodiment, the composition comprises a compound of Formula I wherein $R^1$, $R^2$, and $R^5$ together with the atoms to which they are attached form a quinuclidine ring.

In another embodiment, the composition comprises a compound of Formula I wherein $R^1$ and $R^2$ are carboxyalkyl or alkoxycarbonylalkyl, more particularly the compound is N-(2-hydroxyethyl)-iminodiacetic acid (HEIDA or HIMDA), also named [carboxymethyl-(2-hydroxy-ethyl)-amino]-acetic acid or ethanolamine-N,N-diacetic acid.

In another embodiment, the composition comprises pharmaceutically acceptable salts of compounds of Formula I wherein $R^1$ or/and $R^2$ are carboxyalkyl, and wherein said salts include base addition salts which are formed with inorganic or organic bases. Acceptable salts from inorganic bases include sodium or potassium salts. Acceptable salts from organic bases include salts formed with primary, secondary or tertiary amines including but not limited to diethanolamine, ethanolamine, triethanolamine, dimethylaminoethanol and other amines of Formula I. Preferably $R^1$ and $R^2$ are carboxyethyl and the salt is formed with a base selected from dimethylaminoethanol and triethanolamine.

In another embodiment, the composition comprises at least one compound selected from the preferred compounds:
2-Aziridin-1-yl-ethanol;
1-Methyl-piperidin-3-ol;
1-Ethyl-piperidin-3-ol;
1-Methyl-piperidin-3-ol;
2-Dibutylamino-ethanol;
(1-Methyl-piperidin-2-yl)-methanol;

2-(4-Benzyl-piperazin-1-yl)-ethanol;
1-Aza-bicyclo[2.2.2]octan-3-ol;
2-(Methyl-phenyl-amino)-ethanol;
1-(2-Hydroxy-ethyl)-2,2,6,6-tetramethyl-piperidin-4-ol;
1-Ethyl-pyrrolidin-3-ol;
2-Dibenzylamino-ethanol;
1-Isopropyl-pyrrolidin-3-ol;
2-{[2-(2-Dimethylamino-ethoxy)-ethyl]-methyl-amino}-ethanol;
2-[Bis-(3-methyl-but-2-enyl)-amino]-ethanol;
[Carboxymethyl-(2-hydroxy-ethyl)-amino]-acetic acid;
1-Benzyl-pyrrolidin-3-ol;
2-(Methyl-{4-[2-(4-nitro-phenyl)-vinyl]-phenyl}-amino)-ethanol;
[Bis-(2-hydroxy-ethyl)-amino]-acetic acid;
2-[Bis-(2-hydroxy-ethyl)-amino]-ethanol;
[(2-Hydroxy-ethyl)-methyl-amino]-acetic acid;
[Ethoxycarbonylmethyl-(2-hydroxy-ethyl)-amino]-acetic acid ethyl ester;
[(2-Acetoxy-ethyl)-ethoxycarbonylmethyl-amino]-acetic acid ethyl ester;
[tert-Butoxycarbonylmethyl-(2-hydroxy-ethyl)-amino]-acetic acid tert-butyl ester;
N-Ethyl-2-[ethylcarbamoylmethyl-(2-hydroxy-ethyl)-amino]-acetamide;
2-[Diethylcarbamoylmethyl-(2-hydroxy-ethyl)-amino]-N,N-diethyl-acetamide;
(2-Oxo-morpholin-4-yl)-acetic acid;
(2-Oxo-morpholin-4-yl)-acetic acid ethyl ester;
4-(2-Hydroxy-ethyl)-morpholin-2-one;
2-[Bis-(2H-tetrazol-5-ylmethyl)-amino]-ethanol;
[(2-Hydroxy-ethyl)-(2H-tetrazol-5-ylmethyl)-amino]-acetic acid;
2-[(2-Hydroxy-ethyl)-(2H-tetrazol-5-ylmethyl)-amino]-ethanol;
1,3-Bis-dimethylamino-propan-2-ol;
2-[Bis-(2-hydroxy-ethyl)-amino]-2-hydroxymethyl-propane-1,3-diol;
1,3,5-Tris-(2-hydroxy-ethyl)-[1,3,5]triazinane-2,4,6-trione; and
2-[(2-Amino-ethyl)-(2-hydroxy-ethyl)-amino]-ethanol;
{[2-(Bis-ethoxycarbonylmethyl-amino)-ethyl]-ethoxycarbonylmethyl-amino}-acetic acid;

and isomers, racemic or non-racemic mixtures of isomers, prodrugs or acceptable salts thereof.

In another embodiment, the composition comprises at least one compound of Formula I wherein $R^9$ is not hydrogen; preferably the composition comprises at least one compound of Formula I selected from:
Phosphoric acid tris-(2-dimethylamino-ethyl)ester;
Carbonic acid bis-(2-dimethylamino-ethyl)ester;
Succinic acid bis-(2-dimethylamino-ethyl)ester;
6-Hydroxy-2,5,7,8-tetramethyl-chroman-2-carboxylic acid 2-dimethylamino-ethyl ester;
2-Amino-pentanedioic acid bis-(2-dimethylamino-ethyl) ester;
2-Oxo-propionic acid 2-dimethylamino-ethyl ester; and
3,6-Bis-dimethylaminomethoxy-xanthen-9-one.

and isomers, racemic or non-racemic mixtures of isomers, prodrugs or acceptable salts thereof.

In another embodiment, the composition comprises at least one compound formed by two molecules of Formula I, wherein $R^1$ and $R^2$ are both carboxyalkyl groups complexed to a metal; particularly the composition comprises at least one metal complex compound of Formula Ia,

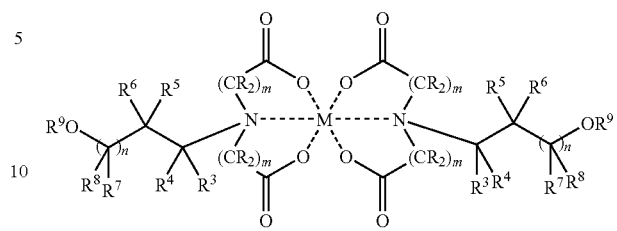

Formula Ia wherein M is a metal, selected from copper (II), zinc(II) and manganese(II) and m, n, R, $R^3$, $R^4$, $R^5$, $R^6$, $R^7$, $R^8$ and $R^9$ are as defined above in group (i); particularly a bivalent transition metal; and preferably the composition comprises at least one compound of Formula Ia, wherein the metal is copper (II), zinc(II) or manganese(II) selected from: bis[[(2-hydroxy-ethyl)-imino]diacetato]-cuprate (II); bis[[(2-hydroxy-ethyl)-imino]-diacetato]-zincate (II); and bis[[(2-hydroxy-ethyl)-imino]-diacetato]-manganate (II), and isomers, racemic or non-racemic mixtures of isomers, or acceptable salts thereof.

In another embodiment, the method of treatment comprises the administration of an effective amount of at least one compound selected from the preferred compounds in admixture with at least one cosmetically acceptable excipient.

In another embodiment, the method comprises a topical composition comprising compounds of any of the Formulae I or Ia for reducing the appearance of skin wrinkles, skin puffiness, dark circles under the eyes, puffiness and sagging in the eye area or jowls, frown lines, expression lines, striae, stretch marks, skin unevenness or roughness, keratoses, hyperkeratinization, loss of skin elasticity, loss of skin tightness, loss of skin firmness, loss of skin recoil from deformation, loss of collagen and elastic fibers, sallowness, blotching, "orange-peel" skin appearance, or bumps and pores.

In another embodiment the method comprises a topical composition comprising compounds of the invention of any of the Formulae I or Ia to reduce the appearance of loss of skin elasticity, skin tightness or skin firmness by lifting or firming the skin. In another embodiment the method comprises a topical composition comprising compounds of the invention of any of the Formulae I or Ia for reducing the appearance of dark circles under the eyes or puffiness or sagging in the eye area.

In another embodiment, the method of treatment comprises administering a topical composition comprising an effective amount of at least one compound represented by a general formula selected from the groups (i), (ii), (iii) and (iv):

i)

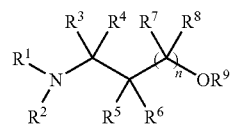

Formula I wherein
- n is 0, 1, or 2;
- $R^1$ is hydrogen, $C_1$-$C_6$-alkyl, $C_2$-$C_{12}$-alkenyl, hydroxyalkyl, carboxyalkyl, alkoxycarbonylalkyl, acetoxyalkyl, aminoalkyl, aminocarbonylalkyl, aryl, arylalkyl, heteroaryl, or heteroarylalkyl;
- $R^2$ is $C_1$-$C_6$-alkyl, $C_2$-$C_{12}$-alkenyl, carboxyalkyl, alkoxycarbonylalkyl, aminoalkyl, acetoxyalkyl, aminocarbonylalkyl, aryl, arylalkyl, heteroaryl, or heteroarylalkyl;
- $R^3$, $R^4$, $R^5$, $R^6$, $R^7$, or $R^3$ are independently of each other hydrogen, $C_1$-$C_6$-alkyl, hydroxyalkyl, or aminoalkyl; and
- $R^9$ is hydrogen, $C_1$-$C_6$-alkyl, phosphoryl, aryl, or acyl;

with the proviso that if $R^1$ is hydrogen, $C_1$-$C_3$-alkyl, or $C_2$-$C_4$-alkanol optionally bearing at least one carboxyl group and $R^2$ is $C_1$-$C_3$-alkyl; then —C($R^3R^4$)—C($R^5R^6$)—(C($R^7R^8$))$_n$—O$R^9$ is not $C_2$-$C_4$-alkanol optionally bearing at least one carboxyl group;

or ii)

Formula I $$R^1\underset{R^2}{\overset{}{N}}-\underset{R^5\ R^6}{\overset{R^3\ R^4}{C}}-\underset{}{\overset{R^7\ R^8}{C}}\!\!-\!\!(\ )_n\!-\!OR^9$$

wherein
- n, $R^1$, and $R^9$ are independently of each other as defined above in group (i); and
- $R^2$ and $R^3$, $R^2$ and $R^5$, $R^3$ and $R^5$, $R^2$ and $R^7$, or $R^2$ and $R^9$ together with the atom or atoms to which they are attached may form a 3- to 7-membered ring optionally incorporating one or more additional NR', O or S groups, wherein R' is $C_1$-$C_6$-alkyl, hydroxyalkyl, phenyl or phenylalkyl wherein the phenyl group is optionally substituted with one or more groups selected from hydroxy, alkyl, halogen, haloalkyl, carboxy, amino and nitro; and wherein the carbon atoms of said 3-to 7-membered ring may be further substituted with at least one $C_1$-$C_6$-alkyl, oxo, hydroxy, or hydroxyalkyl; and the $R^2$, $R^3$, $R^4$, $R^5$, $R^6$, $R^7$, or $R^8$ groups not forming a ring are independently of each other as defined above in group (i);

or iii)

Formula I $$R^1\underset{R^2}{\overset{}{N}}-\underset{R^5\ R^6}{\overset{R^3\ R^4}{C}}-\underset{}{\overset{R^7\ R^8}{C}}\!\!-\!\!(\ )_n\!-\!OR^9$$

wherein
- n, $R^3$, $R^4$, $R^6$, $R^7$, $R^8$, and $R^9$ are as defined above in group (i); and
- $R^1$, $R^2$, and $R^5$ together with the atoms to which they are attached form a bicyclic ring;

or iv)

Formula Ia wherein
- M is a metal;
- m is 1, 2, 3, or 4;
- R is independently hydrogen or $C_1$-$C_6$-alkyl, and
- n, $R^3$, $R^4$, $R^5$, $R^6$, $R^7$, $R^8$, or $R^9$ are as defined above in group (i);

or individual isomers, racemic or non-racemic mixtures of isomers, or acceptable salts or solvates thereof, more particularly the composition comprises N-(2-hydroxyethyl)-iminodiacetic acid, or bis[[(2-hydroxy-ethyl)-imino]diacetato] metal complexes, or salts thereof; and further comprises at least one additional benefit agent selected from sunscreens, retinol, retinoic acid, retinyl ester, retinoyl ester, antioxidants; hydroxyacids; fatty acids; acceptable non-toxic organic salts of zinc or copper optionally derived from naturally occurring amino acids or from hydroxyalkyl acids; botanical extracts; salicylic acid; benzoyl peroxide; antibiotics; antiandrogens; anti-inflammatory agents; ascorbic acid; vitamins B; tocopherols or tocotrienols such as Vitamin E, alpha-tocopherol, beta-tocopherol, or gamma-tocopherol; corticosteroids; or mixtures thereof.

In another embodiment, the method of treatment comprises the administration of a composition comprising an effective amount of at least one compound of any of the Formulae I or Ia with one or more additional acceptable non-toxic organic salts of a metal, such as zinc, copper or magnesium, optionally derived from naturally occurring amino acids, from hydroxyalkyl acids, the latter in particular being sugar-derived acids, or from other cosmetically acceptable acids; more particularly the composition additionally comprises salts of copper (II) or zinc (II) with malonic or gluconic acid.

In yet another aspect, the invention relates to a method of promoting a product by directing the user to apply a topical composition incorporating a compound of any Formulae I or Ia, particularly a composition comprising N-(2-hydroxyethyl)-iminodiacetic acid, or bis[[(2-hydroxy-ethyl)-imino] diacetato] metal complexes, or salts thereof, for reducing the appearance of dermatological conditions, comprising skin wrinkles, skin puffiness, dark circles under the eyes, sagging in the eye area or jowls, frown lines, expression lines, striae, stretch marks, skin unevenness or roughness, keratoses, hyperkeratinization, loss of skin elasticity, loss of skin tightness, loss of skin firmness, loss of skin recoil from deformation, loss of collagen and elastic fibers, sallowness, blotching, "orange-peel" skin appearance, bumps and pores.

In another embodiment, the invention relates to a method of promoting a product by directing the user to apply a topical composition incorporating a compound of any Formulae I or Ia, particularly a composition comprising N-(2-hydroxyethyl)-iminodiacetic acid with one or more non-toxic organic salts of a metal, such as zinc, copper or magnesium, optionally derived from naturally occurring amino acids, from hydroxyalkyl acids, the latter in particular being sugar-derived acids, or from other cosmetically acceptable acids; more particularly the composition additionally comprises salts of copper (II) or zinc (II) with malonic or gluconic acid, for reducing the appearance of dermatological conditions, comprising skin wrinkles, skin puffiness, dark circles under the eyes, sagging in the eye area or jowls, frown lines, expression lines, striae, stretch marks, skin unevenness or roughness, keratoses, hyperkeratinization, loss of skin elasticity, loss of skin tightness, loss of skin firmness, loss of skin recoil from deformation, loss of collagen and elastic fibers, sallowness, blotching, "orange-peel" skin appearance, bumps and pores.

The invention also entails a product comprising instructions directing the user to apply a composition of the invention to the skin for reduction of appearance of dermatological conditions, comprising skin wrinkles, skin puffiness, dark circles under the eyes, sagging in the eye area or jowls, frown lines, expression lines, striae, stretch marks, skin unevenness or roughness, keratoses, hyperkeratinization, loss of skin elasticity, loss of skin tightness, loss of skin firmness, loss of skin recoil from deformation, loss of collagen and elastic fibers, sallowness, blotching, "orange-peel" skin appearance, bumps and pores; particularly to a product comprising a composition incorporating a compound of any of Formulae I or Ia, particularly the composition comprises N-(2-hydroxyethyl)-iminodiacetic acid optionally with a metal salt, preferably a copper (II) or zinc (II) salt; or bis[[(2-hydroxy-ethyl)-imino] diacetato] metal complexes, or salts thereof.

The invention also entails the use of a composition comprising a compound of any of the Formulae I or Ia in the manufacture of a cosmetic for the reduction of appearance of skin wrinkles, skin puffiness, dark circles under the eyes, sagging in the eye area or jowls, frown lines, expression lines, striae, stretch marks, skin unevenness or roughness, keratoses, hyperkeratinization, loss of skin elasticity, loss of skin tightness, loss of skin firmness, loss of skin recoil from deformation, loss of collagen and elastic fibers, sallowness, blotching, "orange-peel" skin appearance, bumps and pores. In a preferred embodiment, the invention entails the use of a composition comprising a compound of any of the Formulae I or Ia in the manufacture of a medicament for the improvement of appearance of loss of skin elasticity, loss of skin tightness, loss of skin firmness by lifting and firming the skin, or reducing the appearance of dark circles and puffiness around and under the eyes, more particularly the composition comprises N-(2-hydroxyethyl)-iminodiacetic acid optionally with a metal salt, preferably a copper (II) or zinc (II) salt; or bis[[(2-hydroxy-ethyl)-imino]diacetato] metal complexes, or salts thereof.

DETAILED DESCRIPTION OF THE INVENTION

Definitions

As used in the present specification, the following words and phrases are generally intended to have the meanings as set forth below, except to the extent that the context in which they are used indicates otherwise.

The term "compounds of Formula I" is intended to encompass the derivatives of the invention as disclosed, and also encompasses isomers, steroisomers, metal complexes especially with Cu, Zn, Mn, Ru, or Fe (herein described as compounds of Formula Ia), prodrugs and acceptable salts thereof. This term encompasses any compound described in the groups (i), (ii), (iii) or (iv) herein and represented by any of the Formulae I or Ia.

Compounds of the present invention are available commercially or can be synthesized as known in the art. Examples 1 to 5 describe the synthesis of some of the compounds of this invention.

The term "acyl" refers to the groups —C(O)—R, wherein R is hydrogen, optionally substituted alkyl, optionally substituted alkyl carbonyl, optionally substituted cycloalkyl, optionally substituted cycloalkylalkyl, optionally substituted aryl, optionally substituted arylalkyl, optionally substituted heteroaryl, optionally substituted heteroarylalkyl, optionally substituted heterocyclyl, or optionally substituted heterocyclylalkyl. This term is exemplified by groups such as acetyl, ethylcarbonyl, cyclopropylcarbonyl, cyclopentylcarbonyl, cyclohexylcarbonyl, 6-hydroxy-2,5,7,8-tetramethyl-chroman-2-carbonyl, 6-hydroxy-2,5,7,8-tetramethyl-chroman-2-ethylcarbonyl, 6-hydroxy-2,7,8-trimethyl-chroman-2-ethyl-carbonyl, —C(O)-Alkyl, —C(O)—O—$(CH_2)_2$—$N(CH_3)_2$, —C(O)—$(CH_2)_2$—C(O)—O—$(CH_2)_2$—$N(CH_3)_2$ or —C(O)—CH(NH)—$(CH_2)_2$—C(O)—O—$(CH_2)_2$—$N(CH_3)_2$.

The term "alkyl" means a monovalent linear or branched saturated hydrocarbon radical, consisting solely of carbon and hydrogen atoms, having from one to twelve carbon atoms inclusive, unless otherwise indicated. Examples of alkyl radicals include, but are not limited to, methyl, ethyl, propyl, isopropyl, sec-butyl, tert-butyl, n-butyl, n-pentyl, n-hexyl, and the like. The term alkyl can also include alkyl groups optionally substituted with hydroxy, cyano, alkyl, alkoxy, thioalkyl, halo, haloalkyl, hydroxyalkyl, nitro, carboxy, alkoxycarbonyl, amino, alkylamino, dialkylamino, aminocarbonyl, carbonylamino, optionally substituted phenylvinyl, heterocyclyl such as tetrazolyl or carbazolyl, aminosulfonyl and/or sulfonylamino unless otherwise indicated.

The term "alkoxy" means a radical —OR, wherein R is an alkyl group as defined herein. Examples of alkoxy radicals include but are not limited to methoxy, ethoxy, propoxy and the like.

The term "alkoxycarbonylalkyl" means a radical -alkylene-C(O)OR, wherein R is a divalent alkyl group as defined herein. Examples of alkoxycarbonyl radicals include but are not limited to methoxycarbonylmethyl, ethoxycarbonylmethyl, methoxycarbonylpropyl, methoxycarbonylethyl and the like.

The term "alkenyl" means the monovalent linear or branched unsaturated hydrocarbon radical consisting solely of carbon and hydrogen atoms, containing at least one double bond and having from 2 to 20 carbons inclusive, unless otherwise indicated. Examples of alkenyl radicals include but are not limited to allyl, 1-propenyl, 2-butenyl, 3-methyl-but-2-enyl also referred to as "prenyl", 3,7-dimethyl-octa-2,6-dienyl also referred to as "geranyl" and the like.

The term "amino" refers to primary, secondary, tertiary, and cyclic amines. Examples of amino are amino, alkylamino, dialkylamino, piperidine, piperazine, and pyrrolidine.

The term "antibiotic" or "antiseptic" agents include but are not limited to but are not limited to mupirocin, neomycin sulfate, bacitracin, polymyxin B, I-ofloxacin, tetracyclines (chlortetracycline hydrochloride, oxytetracycline hydrochloride and tetracycline hydrochoride), clindamycin phosphate, gentamicin sulfate, benzalkonium chloride, benzethonium chloride, hexylresorcinol, methylbenzethonium chloride, phenol, quaternary ammonium compounds, triclosan, tea tree oil, benzoyl peroxide and their pharmaceutically acceptable salts.

The term "aryl" means a monovalent cyclic aromatic hydrocarbon radical consisting of one or more fused rings in which at least one ring is aromatic in nature, which can optionally be substituted with hydroxy, cyano, alkyl, alkoxy, thioalkyl, halo, haloalkyl, hydroxyalkyl, nitro, carboxy, alkoxycarbonyl, amino, alkylamino, dialkylamino, aminocarbonyl, carbonylamino, optionally substituted phenylvinyl, aminosulfonyl and/or sulfonylamino unless otherwise indicated. Examples of aryl radicals include, but are not limited to, phenyl, naphthyl, biphenyl, 2-(4-nitro-phenyl)-vinylphenyl, anthracen-9-one, 1,8-dihydroxy-10H-anthracen-9-one, xanthene-9-one, and the like.

The term "carboxyalkyl" refers to the groups —R—C(O)OH, wherein R is an alkylene group. Examples of carboxyalkyl include but are not limited to carboxymethyl, carboxyethyl, or carboxypropyl, and the like.

The term "cosmetics" includes make-up, foundation, and skin care products. The term "make-up" refers to products that leave color on the face, including foundations, blacks and browns, i.e., mascara, concealers, eye liners, brow colors, eye shadows, blushers, lip colors, and so forth. The term "foundation" refers to liquid, creme, mousse, pancake, compact, concealer, or like products that even out the overall coloring of the skin. Foundation is typically manufactured to work better over moisturized and/or oiled skin. The term "skin care products" refers to products used to treat or otherwise care for, moisturize, improve, or clean the skin. Products contemplated by the phrase "skin care products" include, but are not limited to, adhesives, bandages, anhydrous occlusive moisturizers, antiperspirants, facial wash cleaners, cold cream, deodorants, soaps, occlusive drug delivery patches, powders, tissues, wipes, solid emulsion compact, anhydrous hair conditioners, medicated shampoos, scalp treatments and the like.

The term "cosmetically-acceptable" or "dermatologically-acceptable," as used herein, means that the compositions or components thereof so-described are suitable for use in contact with human skin without undue toxicity, incompatibility, instability, allergic response, or the like.

As used herein, the term "cosmetically acceptable carrier", "cosmetically acceptable excipient", "dermatologically acceptable carrier" or "dermatologically acceptable excipient" includes any and all solvents, dispersion media, coatings, antibacterial and antifungal agents, isotonic and absorption delaying agents and the like. The use of such media and agents for cosmetically active substances is well known in the art. Except insofar as any conventional media or agent is incompatible with the active ingredient, its use in the cosmetic compositions is contemplated. Supplementary active ingredients can also be incorporated into the compositions.

The term "effective amount" refers to that amount of a compound of the present invention that is sufficient to effect treatment, as defined below, when administered to a mammal in need of such treatment. The effective amount will vary depending upon the subject and disease condition being treated, the weight and age of the subject, the severity of the disease condition, the particular compound chosen, the dosing regimen to be followed, and the like, all of which can readily be determined by one of ordinary skill in the art.

The term "heteroaryl" refers to an aromatic cyclic hydrocarbon group having 3 to 15 carbon atoms and about one to four heteroatoms, selected from nitrogen, sulfur and/or oxygen with at least one ring. Such heteroaryl groups can have a single ring or multiple condensed rings. Preferred heteroaryl groups are tetrazole, triazole, imidazole, thiazole, pyrazole, pyridine, pyrimidine, pyrrole, furan, thiophene, oxazole, isoxazole, thiazole, isothiazole, benzimidazole, benzoxazole, benzofuran, benzopyran, benzothiophene, indole, indazole, quinoline, etc. This term is exemplified by tetrazole.

The term "α-hydroxyacids" refers to adjunct ingredients in many embodiments and refers to the general class of organic compounds containing at lest one hydroxy group and at least one carboxy group, and wherein at least on hydroxy group is located on the alpha carbon atom. The compounds may contain other functional groups including additional hydroxy and carboxy moieties. Preferred alpha-hydroxy acids are structurally able to penetrate the skin well, and thus have a backbone from one to three carbon atoms. Preferred are glycolic and/or lactic acid. Alpha-hydroxy acids are typically present in amounts ranging from 1% to 10%, preferably from 3% to 7% of the total composition.

The term "personal care products" refers to health and cosmetic beauty aid products generally recognized as being formulated for beautifying and grooming the skin and hair. For example, personal care products include sunscreen products (e.g., lotions, skin creams, etc.), cosmetics, toiletries, and over-the-counter therapeutical products intended for topical usage.

The term "phosphoryl" refers to the group —P(O)(OR)$_2$, where R is independently selected from hydrogen, alkyl, aminoalkyl, and aryl, which group is sometimes also referred to as "phosphono", "phosphate" or "phosphoric acid". This term is exemplified by bis-(2-dimethylamino-ethyl)phosphoryl.

The term "prodrug" refers to an inactive form of a compound which must be metabolized in vivo, e.g., by biological fluids or enzymes, by a subject after administration into an active form of the compound in order to produce the desired pharmacological effect. The prodrug can be metabolized before absorption, during absorption, after absorption, or at a specific site. Prodrug forms of compounds may be utilized for example, to improve bioavailability, improve subject acceptability such as masking or reducing unpleasant characteristics such as a bitter taste, odor, or gastrointestinal irritability, alter solubility, provide for prolonged or sustained release or delivery, improve ease of formulation, or provide site-specific delivery of the compound. Reference to a compound herein includes prodrug forms of a compound.

"Regulating skin condition" includes regulating the appearance of a skin condition, including visible and/or tactile discontinuities in skin such as, but not limited to, skin wrinkles, elasticity or the sagging of skin, oily skin, puffiness of skin under the eyes, and striae or stretch marks. Regulating skin condition may involve improving skin appearance and/or feel. Regulating skin condition may include lifting and improving the tone and firmness of the skin.

"Regulating the signs of skin aging" includes cosmetically regulating the appearance of one or more of such signs of skin aging as defined herein.

"Signs of skin aging" include, but are not limited to, all outward visibly and tactilely perceptible manifestations as well as any other macro or micro effects due to skin aging. Such signs may be induced or caused by intrinsic factors or extrinsic factors, e.g., chronological aging and/or environmental damage (e.g., sunlight, UV, smoke, ozone, pollutants, stress, etc.). These signs may result from processes which include, but are not limited to, the development of textural discontinuities such as wrinkles, including both fine superficial wrinkles and coarse deep wrinkles, skin lines, facial frown lines, expression lines, rhytides, dermatoheliosis, dark circles under the eyes, photodamage, premature skin aging, crevices, bumps, pits, large pores (e.g., associated with adnexal structures such as sweat gland ducts, sebaceous glands, or hair follicles), "orange-peel" skin appearance, dryness, scaliness, flakiness and/or other forms of skin unevenness or roughness; blemishes such as acne, pimples, breakouts; excess skin oil problems such as over production of sebum, oiliness, facial shine, foundation breakthrough; abnormal desquamation (or exfoliation) or abnormal epidermal differentiation (e.g., abnormal skin turnover) such as scaliness, flakiness, keratoses, hyperkeratinization; inadequate skin moisturization (or hydration) such as caused by skin barrier damage, environmental dryness; loss of skin elasticity (loss and/or inactivation of functional skin elastin) such as elastosis, sagging (including puffiness and dark circles in the eye area and jowls), loss of skin firmness, loss of skin tightness, loss of skin recoil from deformation; loss of muscle tone, non-melanin skin discoloration such as undereye circles, blotching (e.g., uneven red coloration due to, e.g., rosacea), sallowness (pale color), discoloration caused by telangiectasia or spider vessels; melanin-related hyperpigmented (or unevenly pigmented) skin regions such as age spots (liver spots, brown spots) and freckles; post-inflammatory hyperpigmentation such as that which occurs following an inflammatory event (e.g., as an acne lesion, in-grown hair, insect/spider bite or sting, scratch, cut, wound, abrasion, and the like); atrophy such as, but not limited to, that associated with aging or steroid use; other histological or microscopic alterations in skin components such as ground substance (e.g., hyaluronic acid, glycosaminoglycans, etc.), collagen breakdown and structural alterations or abnormalities (e.g., changes in the stratum corneum, dermis, epidermis, the skin vascular system such as telangiectasia or spider vessels); tissue responses to insult such as itch or pruritus; and alterations to underlying tissues (e.g., subcutaneous fat, cellulite, muscles, septae, and the like), especially those proximate to the skin.

The terms "skin condition", "dermatologic condition", and "dermatological condition" are used interchangeably.

The term "sunscreen" may include but is limited to organic or inorganic sunscreens, such as, methoxycinnamate, oxybenzone, avobenzone, and the like, sun blocks such as titanium oxide and zinc oxide, and skin protectants or mixtures thereof.

The term "treatment" or "treating" as used herein means the reduction in appearance of skin imperfections irrelevant of the mechanism of action.

The term "topical application", as used herein, means to apply or spread the compositions of the present invention onto the surface of the skin and/or hair.

The term "tocopherols or tocotrienols", as used herein encompasses a family of molecules characterized by a 6-chromanol ring structure and a side chain at the 2-position. Tocopherols possess a 4',8',12'-trimethyltridecyl phytol side chain, tocotrienols possess an unsaturated phytol side chain. As used herein the term tocopherol or tocotrienols means alpha-, beta-, gamma- or delta-, epsilon- and zeta-tocopherol or tocotrienols, (see *The Merck Index* (1996), Merck & Co. Whitehouse Sation. N.J. 1620-1621 and 1712, and references sited therein) as well as Vitamin E. The term tocopherol also includes cosmetically acceptable esters, for example tocopherol acetate, tocopherol lineate, tocopherol stearate. The term tocopherol also includes mixtures of tocopherols, tocotrienols and/or stereoisomers as well as enriched compositions comprising at least 50% of any tocopherol or tocotrienol. The tocopherols and tocotrienols can be of natural or synthetic origin.

The term "retinoids" as used herein, means retinol, retinyl palmitate, retinyl linoleate, retinoic acid or esters, as well as synthetic or natural Vitamin A. The term "retinol" includes the following isomers of retinol: all-trans-retinol, 13-cis-retinol, 11-cis-retinol, 9-cis-retinol, 3,4-didehydro-retinol. Preferred isomers are all-trans-retinol, 13-cis-retinol, 3,4-didehydro-retinol, 9-cis-retinol. Retinyl ester is an ester of retinol, as defined above. Retinyl esters suitable for use in the present invention are $C_1$-$C_{30}$ esters of retinol, preferably $C_2$-$C_{20}$ esters, and most preferably $C_2$-$C_3$, and $C_{16}$ esters because they are more commonly available. Some preferred esters for use in the present invention may be selected from, retinyl palmitate, retinyl acetate, retinyl propionate and retinyl linoleate. Retinoyl ester is an ester of retinoic acid. Retinoyl esters suitable for use in the present invention include $C_1$-$C_{30}$ esters of retinoic acid, preferably $C_2$-$C_{20}$ esters and most preferably $C_2$-$C_3$ and $C_{16}$ esters. Some preferred retinoyl esters for use in the present invention comprise retinoyl linoleate, retinoyl palmitate, retinoyl oleate, retinoyl ascorbate, and retinoyl linoleate.

Utility, Testing and Administration

General Utility

The compounds, formulations and methods of the present invention may be useful in the reduction of appearance of skin conditions comprising skin wrinkles, skin puffiness, dark circles under the eyes, sagging in the eye area or jowls, frown lines, expression lines, striae, stretch marks, skin unevenness or roughness, keratoses, hyperkeratinization, loss of skin elasticity, loss of skin tightness, loss of skin firmness, loss of skin recoil from deformation, loss of collagen and elastic fibers, sallowness, blotching, "orange-peel" skin appearance, bumps and pores.

As the skin ages, the dermis decreases in density and becomes relatively acellular and avascular. Throughout adult life, the total amount of collagen decreases about one percent per year. The collagen fibers thicken, becoming less soluble, have less capacity for swelling, and become more resistant to digestion by collagenase. There are also structural aberrations in the elastic fibers of the reticular dermis that contribute to skin sagging. The regression of the subepidermal elastic network may contribute to cutaneous laxity and the subtle wrinkled appearance prevalent on sun-protected skin of the elderly. Atrophy of the dermis and subcutaneous fat also plays an important role in the formation of wrinkles. The compounds of the present invention may be useful in the lifting of skin, thus giving it a more youthful appearance and in reducing the appearance of signs of skin aging, as described herein.

In addition, compositions and methods of the present invention may be useful treating muscle conditions associated with loss of muscle tone, such as sagging of tissue around the eves, hanging of tissue from the mandibular region, nasolabial folds, sagging of pectoralis muscles resulting in sagging of the chest and sagging of triceps resulting in sagging of the upper arms.

The compositions of the present invention may be useful for reducing the appearance of signs of skin aging, as described herein that may be induced or caused by internal and/or external factors, including but not limited to loss of skin elasticity, loss of skin tightness or loss of skin firmness.

The compositions of the present invention may be useful for reducing the appearance of puffer or pouch-like skin, bags, rings or dark circles beneath or around the eyes. These conditions may be caused for example by aging, environmental factors, stress, lack of sleep, overindulgence with alcohol, or various diseases It is to be understood that the present invention is not to be limited to regulation of the appearance of "signs of skin aging" that arise due to the above-mentioned mechanisms associated with skin aging, but is intended to include regulation of the appearance of such signs irrespective of their mechanism of origin.

Testing

This section describes how compositions incorporating compositions of the present invention are selected based on in vitro assays' activity and in vivo evaluations, and used as therapeutic interventions in dermatological indications Cell injury protection can be evaluated in cell culture using the procedure used to induce high glutamate-induced oxidative stress (HGOS) in dopaminergic cell lines. Using this assay the potency and efficacy of test articles against HGOS cell injury and cell death can be established in a high throughput manner, as described in Examples. Certain compounds of the present invention showed protection against HGOS cell injury and cell death at an $EC_{50}$ less than 50 µM, preferably less than 10 µM.

Information on cell motility can be assessed by an electrochemical-based system, known as the Electric Cell Impedance Sensing ("ECIS™") system sold by Applied Biophysics, Inc. (Troy, N.Y.). In the ECIS™ assay system, two electrodes are lithographed onto the surface of a lexan slide and positioned within a chamber that holds aqueous media. Cells in this media can attach to a sensing electrode and to the surrounding surface of the slide. A 1 volt a.c. current passes through the culture media that functions as an electrolyte, and a lock-in amplifier measures current flow through this circuit. This measurement provides data on the initial resistance of the system and, more importantly, any changes to current flow on the electrode that occurs over time. Due to the relatively small size of the electrode, resistance at the sensing electrode predominates in the system. Any activity that affects the adherence of cells to the electrodes will alter the measured electrical resistance in the system. The degree of changes in cell motility will be reflected by changes in the measured electrode resistance as the extent of interaction between the cells and the electrode surface changes.

Skin elasticity can be measured using a ballistometer. This is a pendulum that is dropped from a fixed height onto the skin surface. It measures the ability of the skin to absorb mechanical energy by analyzing the rebound pattern displayed by a probe as it strikes the skin. The elastic components of the skin store the kinetic energy generated by the striking of the probe and cause the probe to rebound upon release. Smaller rebounds, with less kinetic energy, result when the probes strikes softer skin, bigger bounces occur from more elastic skin.

Dermatologist experts trained in visual and tactile evaluations can use their finger to investigate the skin softness and firmness by touching its surface softly or by pressing down to detect any presence of cutaneous changes and ageing signs of the skin by grading on a semi-structured scale.

Replacing the human finger with a robot one to measure skin stiffness with a probe loaded with a tactile vibration sensor and displacement sensor has been described by Su Sasai et al, *Skin Research and Technology*, 1999, 5, 237-246.

Skin thickness and tissue density can be assessed with ultrasound using a B scanning probe. Several ultrasound images on each test site are stored in a computer to be analyzed via DIA for overall changes in skin density and skin thickness.

Skin smoothness can be usually measured on a silicone elastomer replica using a mechanical stylus instrument, laser profilometry or a shadowing method, such as the Dermatest™ UB16 optical measuring system.

The in vivo measurements of the skin rheological properties using non-invasive techniques made it possible to evaluate changes caused by a cosmetic preparation to the viscoelastic properties of the skin over a period of time. The skin was crossed by an acoustical shockwave and the Resonance Running Time Measurement (RRTM) was calculated using for example the Reviscometer RVM600, which allowed relation between body mass index and elasticity as well as photoageing. Loose or sagging skin generally poses considerable resistance to the wave propagation, thus resulting in a relatively high RRTM. In contrast, sound waves are able to travel over firm skin more easily; hence firmer skin has a lower RRTM.

The ability of the inventive compounds to reduce dark circles and puffiness around the eyes can be evaluated by an expert grader and the panelists recruited for the study.

Administration

Generally, the compounds of the present invention are administered topically at an effective dosage, e.g., a dosage sufficient to provide treatment for the disease states previously described. Generally dosage forms or compositions containing active ingredient in the range of 0.005% to 50%, preferably, 0.01 to 10% and more preferably 0.05% to 1% by weight with the balance made up from non-toxic carrier may be prepared.

Administration of the compounds of any of the Formulae I or Ia can be via any of the accepted modes of administration for agents that serve similar utilities, preferably by topical administration, i.e. by spreading, spraying, etc. onto the surface of the skin or hair.

The compositions of the present invention may be suitable for reducing the appearance of a skin condition against the adverse effects of aging, preferably in personal care products.

Compounds and methods of the invention may be employed in any skin care application where decreased wrinkling or sagging of the skin is desired. For example, compounds and compositions of the invention may be incorporated into leave-on and rinse-off acne preparations, facial milks and conditioners, shower gels, foaming and non-foaming facial cleansers, cosmetics, hand and body lotions, leave-on moisturizers, cosmetic and cleaning wipes, or the like. Generally, for dermal applications, topical administration is preferred; however, systemic administration may also be possible.

Compositions of the present invention may also be used in cosmetic compositions. Cosmetic compositions of the present invention are ideally suited for use in treating the skin and lips, especially in the form of a lipstick or lip balm for applying to the lips a permanent or semi-permanent color, ideally with a gloss or luster finish. The cosmetic compositions may also be used in treating the skin with a skin care agent for protection against exposure to adverse weather, including the wind and rain, dry and/or hot environments, environmental pollutants (e.g., ozone, smoke, and the like), or exposure to excessive doses of sunlight. Certain compositions may also be useful in moisturizing and/or conditioning for the hair and skin, improved skin feel, regulating skin texture, and reducing fine lines and wrinkles.

The cosmetic compositions may accordingly be applied to the skin in the traditional manner with or without a conventional holder or applicator to provide a decorative and/or protective film thereto.

The compositions of this invention may be in the form of emulsions, such as creams, lotions and the like. Such compositions may have more than one phase and may include surface active agents which enable multiphase emulsions to be manufactured.

The compositions may typically include a conventional carrier or excipient, and a compound of the present invention or a therapeutically acceptable salt thereof. Such a suitable carrier is adequate for topical use. It is not only compatible with the active ingredients described herein, but will not introduce any toxicity and safety issues. An effective and safe carrier may vary from about 50% to about 99% by weight of the compositions of this invention, more preferably from about 75% to about 99% of the compositions and most preferably from about 85% to about 95% by weight of the compositions. In addition, these compositions may include other medicinal agents, therapeutical agents, carriers, adjuvants, and the like. Some preferred additional agents may include sunscreens; retinoids; antioxidants; hydroxyacids; fatty acids, acceptable non-toxic organic salts of metal derived from naturally occurring amino acids or from hydroxyalkyl acids; botanical extracts, salicylic acid, benzoyl peroxide, antibiotics, antiandrogens, anti-inflammatory agents, ascorbic acid, vitamins B, tocopherols or tocotrienols, corticosteroids, and mixtures thereof.

Dermatologic formulations of the present invention may typically comprise a derivative of any of the present invention and optionally, a polar solvent. Solvents suitable for use in the formulations of the present invention include any polar solvent capable of dissolving the derivative of the invention. Suitable polar solvents may include: water; alcohols (such as ethanol, propyl alcohol, isopropyl alcohol, hexanol, and benzyl alcohol); polyols (such as propylene glycol, polypropylene glycol, butylene glycol, hexylene glycol, malitol, sorbitol, and glycerine); and panthenol dissolved in glycerine, flavor oils and mixtures thereof. Mixtures of these solvents can also be used. Exemplary polar solvents may be polyhydric alcohols and water. Examples of solvents may include glycerine, panthenol in glycerine, glycols such as propylene glycol and butylene glycol, polyethylene glycols, water and mixtures thereof. Additional polar solvents for use may be alcohols, glycerine, panthenol, propylene glycol, butylene glycol, hexylene glycol and mixtures thereof.

An emollient may also be added to the cosmetic/dermatological compositions of the present invention. The emollient component can comprise fats, oils, fatty alcohols, fatty acids and esters which aid application and adhesion, yield gloss and most importantly provide occlusive moisturization. Suitable emollients for use may be isostearic acid derivatives, isopropyl palmitate, lanolin oil, diisopropyl dimerate, maleated soybean oil, octyl palmitate, isopropyl isostearate, cetyl lactate, cetyl ricinoleate, tocopheryl acetate, acetylated lanolin alcohol, cetyl acetate, phenyl trimethicone, glyceryl oleate, tocopheryl linoleate, wheat germ glycerides, arachidyl propionate, myristyl lactate, decyl oleate, propylene glycol ricinoleate, isopropyl linoleate, pentaerythrityl tetrastearate, neopentylglycol dicaprylate/dicaprate, hydrogenated cocoglycerides, isononyl isononanoate, isotridecyl isononanoate, myristyl myristate, triisocetyl citrate, cetyl alcohol, octyl dodecanol, oleyl alcohol, panthenol, lanolin alcohol, linoleic acid, linolenic acid, sucrose esters of fatty acids, octyl hydroxystearate and mixtures thereof. Examples of other suitable emollients can be found in the Cosmetic Bench Reference, pp. 1.19-1.22 (1996), incorporated herein by reference. Suitable emollients may include polar emollient emulsifiers (such as linear or branched chained polyglycerol esters) and non-polar emollients. The emollient component typically may comprise from about 1% to about 90%, preferably from about 10% to about 80%, more preferably from about 20% to about 70%, and most preferably from about 40% to about 60%, of the cosmetic composition.

By "polar emollient," as used herein, is meant any emollient emulsifier having at least one polar moiety and wherein the solubility (at 30 degrees C.) of the cytoprotective derivative compound in the polar emollient is greater than about 1.5%, preferably greater than about 2%, more preferably greater than about 3%. Suitable polar emollients may include, but are not limited to, polyol ester and polyol ethers such as linear or branched chained polyglycerol esters and polyglycerol ethers. Nonlimiting examples of such emollients may include PG3 diisosterate, polyglyceryl-2-sesquiisostearate, polyglyceryl-5-distearate, polyglyceryl-10-distearate, polyglyceryl-10-diisostearate, acetylated monoglycerides, glycerol esters, glycerol tricaprylate/caprate, glyceryl ricinoleate, glyceryl isostearate, glyceryl myristate, glyceryl linoleate, polyalkylene glycols such as PEG 600, monoglycerides, 2-monolaurin, sorbitan esters and mixtures thereof.

By "non-polar emollient," as used herein, means any emollient emulsifier possessing no permanent electric moments. Suitable non-polar emollients may include, but are not limited to, esters and linear or branched chained hydrocarbons. Non-limiting examples of such emollients may include isononyl isononanoate, isopropyl isostearate, octyl hydroxystearate, diisopropyl dimerate, lanolin oil, octyl palmitate, isopropyl palmitate, pariffins, isoparrifins, acetylated lanolin, sucrose fatty acid esters, isopropyl myristate, isopropyl stearate, mineral oil, silicone oils, dimethicone, allantoin, isohexadecane, isododecane, petrolatum, and mixtures thereof. The solubility of the compound in polar or non-polar emollients may be determined according to methods known in the art.

Suitable oils include esters, triglycerides, hydrocarbons and silicones. These can be a single material or a mixture of one or more materials. They may normally comprise from 0% to about 100%, preferably from about 5% to about 90%, and most preferably from about 70% to about 90% of the emollient component.

Oils that act as emollients also impart viscosity, tackiness, and drag properties to cosmetic compositions such as lipstick. Examples of suitable oils may include caprylic triglycerides; capric triglyceride; isostearic triglyceride; adipic triglyceride; propylene glycol myristyl acetate; lanolin; lanolin oil; polybutene; isopropyl palmitate; isopropyl myristate; isopropyl isostearate; diethyl sebacate; diisopropyl adipate; tocopheryl acetate; tocopheryl linoleate; hexadecyl stearate; ethyl lactate; cetyl oleate; cetyl ricinoleate; oleyl alcohol; hexadecyl alcohol; octyl hyroxystearate; octyl dodecanol; wheat germ oil; hydrogenated vegetable oils; castor oil; petrolatum; modified lanolins; branched-chain hydrocarbons; alcohols and esters; corn oil; cottonseed oil; olive oil; palm kernel oil; rapeseed oil; safflower oil; jojoba oil; evening primrose oil; avocado oil mineral oil, shea butter, octylpalmitate, maleated soybean oil, glycerol trioctanoate, diisopropyl dimerate, and volatile and non-volatile silicone oils including phenyl trimethicone.

Suitable oils for use herein may be acetylglycerides, octanoates, and decanoates of alcohols and polyalcohols, such as those of glycol and glycerol, the ricinoleates of alcohols and polyalcohols such as cetyl ricinoleate, PG-3 diisostearate, polyglycerol ethers, polyglyerol esters, caprylic triglycerides, capric triglycerides, isostearic triglyceride, adipic triglyceride, phenyl trimethicone, lanolin oil, polybutene, isopropyl palmitate, isopropyl isostearate, cetyl ricinoleate, octyl dodecanol, oleyl alcohol, hydrogenated vegetable oils, castor oil, modified lanolins, octyl palmitate, lanolin oil, maleated soybean oil, cetyl ricinoleate, glyceryl trioctanoate, diisopropyl dimerate, synthetic lanolin derivatives and branched chain alcohols, sucrose esters of fatty acids, octyl hydroxystearate and mixtures thereof.

Preferably, the oils used may be selected such that the majority (at least about 75%, preferably at least about 80% and most preferably at least about 99%) of the types of oils used have solubility parameters that do not differ by more than from about 1 to about 0.1, preferably from about 0.8 to about 0.1.

A surfactant may also be added to compositions of the invention, in order to confer beneficial cosmetic or application properties. Surfactants suitable for use may be those which can form emulsions and/or association structures. Surfactant emulsifier can be from 0% to about 20% of the formulation, preferably from 0% to about 15% and most preferably from about 1% to about 10%. Examples of suitable emulsifiers can be found in U.S. Pat. No. 5,085,856 to Dunphy et al., and U.S. Pat. No. 5,688,831 to El-Nokaly et al. Examples of other suitable emulsifiers can be found in Cosmetic Bench Reference, pp. 1.22, 1.24-1.26 (1996), all of which are incorporated herein by reference.

Examples of surface active agents which may be used in the compositions of this invention include sodium alkyl sulfates, e.g., sodium lauryl sulfate and sodium myristyl sulfate, sodium N-acyl sarcosinates, e.g., sodium N-lauroyl sarcosinate and sodium N-myristoyl sarcosinate, sodium dodecylbenzenesulfonate, sodium hydrogenated coconut fatty acid monoglyceride sulfate, sodium lauryl sulfoacetate and N-acyl glutamates, e.g., N-palmitoyl glutamate, N-methylacyltaurin sodium salt, N-methylacylalanine sodium salt, sodium a-olefin sulfonate and sodium dioctylsulfosuccinate; N-alkylaminoglycerols, e.g., N-lauryl-diamino-ethylglycerol and N-myristyldiaminoethylglycerol, N-alkyl-N-carboxymethylammonium betaine and sodium 2-alkyl-1-hydroxyethylimidazoline betaine; polyoxyethylenealkyl ether, polyoxyethylenealkylaryl ether, polyoxyethylenelanolin alcohol, polyoxyethyleneglyceryl monoaliphatic acid ester, polyoxyethylenesorbitol aliphatic acid ester, polyoxyethylene aliphatic acid ester, higher aliphatic acid glycerol ester, sorbitan aliphatic acid ester, Pluronic type surface active agent, and polyoxyethylenesorbitan aliphatic acid esters such as polyoxyethylenesorbitan monooleate and polyoxyethylenesorbitan monolaurate. Emulsifier-type surfactants know to those of skill in the art should be used in the compositions of this invention.

Also useful herein may be surfactants that form association structures, preferably lamellar or hexagonal liquid crystals, at ambient temperature when mixed with a polar solvent. Ambient temperature/room temperature as used herein typically may mean about 20° C. Generally ambient temperature can range from about 18° C. to about 27° C., preferably from about 20° C. to about 25° C., depending on such variables as geographical location, i.e. sub-tropical vs. temperature regions. One of ordinary skill in art may readily be able to determine if association structures form at ambient temperatures. The surfactants suitable for use generally have a Krafft point at or below about ambient temperature about 20° C. or generally at or below about 18° C. to about 27° C., preferably at or below from about 20° C. to about 25° C.

The definition of Krafft point is well known in the art and one of ordinary skill in the art can readily determine a surfactant's Krafft point. In general terms, Krafft point is the melting point of the hydrocarbon chains of the surfactants. It can also be expressed as the temperature at which the solubility of an association colloid in water suddenly increases because critical micelle concentration is exceeded and micelles form.

Examples of surface active agents which may be used in the compositions of this invention include sodium alkyl sulfates, e.g., sodium lauryl sulfate and sodium myristyl sulfate, sodium N-acyl sarcosinates, e.g., sodium N-lauroyl sarcosinate and sodium N-myristoyl sarcosinate, sodium dodecylbenzenesulfonate, sodium hydrogenated coconut fatty acid monoglyceride sulfate, sodium lauryl sulfoacetate and N-acyl glutamates, e.g., N-palmitoyl glutamate, N-methylacyltaurin sodium salt, N-methylacylalanine sodium salt, sodium a-olefin sulfonate and sodium dioctylsulfosuccinate; N-alkylaminoglycerols, e.g., N-lauryldiaminoethylglycerol and N-myristyldiaminoethylglycerol, N-alkyl-N-carboxymethylammonium betaine and sodium 2-alkyl-1-hydroxyethylimidazoline betaine; polyoxyethylenealkyl ether, polyoxyethylenealkylaryl ether, polyoxyethylenelanolin alcohol, polyoxyethyleneglyceryl monoaliphatic acid ester, polyoxyethylenesorbitol aliphatic acid ester, polyoxyethylene aliphatic acid ester, higher aliphatic acid glycerol ester, sorbitan aliphatic acid ester, Pluronic type surface active agent, and polyoxyethylenesorbitan aliphatic acid esters such as polyoxyethylenesorbitan monooleate and polyoxyethylenesorbitan monolaurate. Emulsifier-type surfactants know to those of skill in the art should be used in the compositions of this invention.

In preparing a sample combination of surfactant and polar solvent to demonstrate the ability to form association structures, the surfactant needs to be sufficiently soluble in the polar solvent such that an association structure can form at ambient temperature. One of ordinary skill in the art is capable of determining compatible interactions.

Any surfactant which forms association structures at ambient temperature and is suitable for use in cosmetics may be suitable for use herein. Surfactants suitable for use in cosmetics do not present dermatological or toxicological problems. Anionic surfactants, nonionic surfactants, cationic surfactants, amphoteric surfactants and mixtures thereof may be suitable for use. Preferably anionic surfactants, nonionic surfactants, cationic surfactants, amphoteric surfactants and mixtures thereof having a Krafft point at or below about ambient temperature are used. More preferably, nonionic surfactants, cationic surfactants, amphoteric surfactants and mixtures thereof having a Krafft point at or below about ambient temperature are used.

The surfactants can be used at levels from about 4% to about 97%, preferably from about 5% to about 95%, more preferably from about 20% to about 90% and most preferably from about 30% to about 70% of the association structure.

The cosmetic compositions of this invention may contain one or more materials, herein singly or collectively referred to as a "solidifying agent", that are effective to solidify the particular liquid base materials to be used in a cosmetic composition. (As used herein, the term "solidify" refers to the physical and/or chemical alteration of the liquid base material so as to form a solid or semi-solid at ambient conditions, i.e., to form a final composition that has a stable physical structure and can be deposited on the skin under normal use conditions.) As is appreciated by those skilled in the art, the selection of the particular solidifying agent for use in the cosmetic compositions will depend upon the particular type of composition desired, i.e., gel or wax-based, the desired rheology, the liquid base material used and the other materials to be used in the composition. The solidifying agent can be preferably present at a concentration of from about 0 to about 90%, more preferably from about 1 to about 50%, even more preferably from about 5% to about 40%, most preferably from about 3% to about 20%.

The wax cosmetic stick embodiments of this invention preferably may contain from about 5% to about 50% (by weight) of a waxy solidifying agent. By the term "waxy solidifying agent," as used herein, is meant a solidifying material having wax-like characteristics. Such waxy materials may also serve as emollients. Among the waxy materials useful herein are the high melting point waxes, i.e., having a melting point of from about 65° C. to about 1250 C., such as beeswax, spermaceti, carnauba, baysberry, candelilla, montan, ozokerite, ceresin, paraffin, synthetic waxes such as Fisher-Tropsch waxes, microcrystalline wax, and mixtures thereof. Ceresin, ozokerite, white beeswax, synthetic waxes, and mixtures thereof, are among those useful herein are disclosed in U.S. Pat. No. 4,049,792, Elsnau, issued Sep. 20, 1977, herein incorporated by reference in its entirety). Low melting waxes, having a melting point of from about 370 C. to about 75° C., may be preferred for use in the wax stick embodiments of this invention. Wax stick embodiments of this invention, which contain volatile silicone oils as a liquid base material, preferably contain from about 10% to about 35%, more preferably from about 10% to about 20% (by weight), of a low-melting wax. Such materials include fatty acids, fatty alcohols, fatty acid esters and fatty acid amides, having fatty chains of from about 8 to about 30 carbon atoms, and mixtures thereof. Wax-like materials include cetyl alcohol, palmitic acid, stearyl alcohol, behenamide, sucrose esters of tallow fatty acids, mono and di-fatty acid esters of polyethylene glycol, and mixtures thereof. Stearyl alcohol, cetyl alcohol, and mixtures thereof, are preferred. Additional fatty acids, fatty alcohols, and other wax-like materials useful in this invention are also well known in the art.

EXAMPLES

The following preparations and examples are given to enable those skilled in the art to more clearly understand and to practice the present invention. They should not be considered as limiting the scope of the invention, but merely as being illustrative and representative thereof.

Example 1

Preparation of bis[[(2-hydroxy-ethyl)-imino]-diacetato]-cuprate (II)

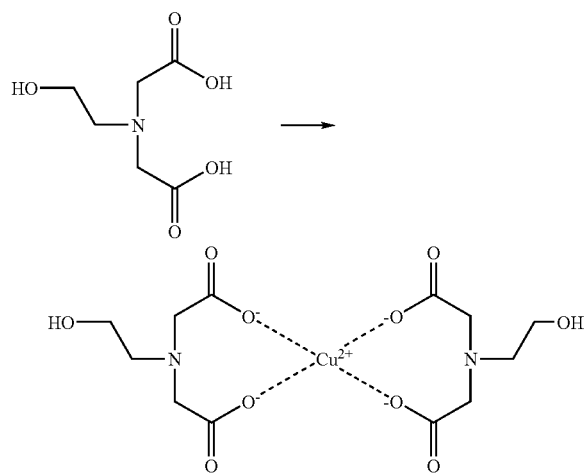

To a stirred solution of N-(2-hydroxyethyl)-iminodiacetic acid (1.0 g, 5.6 mmol) in 20 mL of water was added 2 N sodium hydroxide solution until the solid completely dissolved. A solution of $CuBr_2$ (0.63 g, 2.8 mmol) in 10 mL of MeOH was then added dropwise to the solution, and blue precipitate was formed in a few minutes. The reaction mixture was stirred for 4 h at room temperature. The blue solid was filtered and dried under high vacuum for 72 h (0.94 g).

UV-Vis Spectroscopy: Solution of $Cu^{2+}$ complex, acid and $CuBr_2$ were prepared in a mixed solvent of 0.1 M pH 7.0 phosphate buffer and MeOH (2:1, v/v). The absorption spectra were recorded in the 200-900 nm range against the solvent blank at room temperature. $Cu^{2+}$ complex shows strong absorption in the visible range with a maximum at 740 nm. At the same concentration (16 mM), N-(2-hydroxyethyl)-iminodiacetic acid has no absorption above 270 nm, and $CuBr_2$ has a weak absorption at 690 nm with poor solubility in the solvent.

Mass analysis suggests that $Cu^{2+}$ complex contain N-(2-hydroxyethyl)-iminodiacetic acid at m/z 178.1 ($M+H^+$) and 200.1 ($M+Na^+$).

Example 2

Preparation of bis[[(2-hydroxy-ethyl)-imino]-diacetato]-zincate(II)

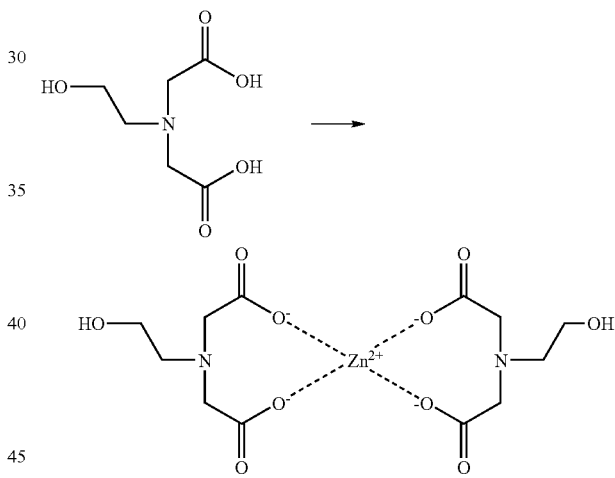

To a stirred solution of N-(2-hydroxyethyl)-iminodiacetic acid (1.0 g, 5.6 mmol) in 20 mL of water was added two equivalents of sodium hydroxide (0.453 g, 11.2 mmol) (pH≈8). A solution of $ZnCl_2$ (0.386 g, 2.8 mmol) in 20 mL of MeOH was then added, and the reaction mixture was allowed to stir at room temperature for 15 h. After the solvent was removed by rotary evaporation, the residue was lyophilized and washed with methanol to give a white solid (1.21 g).

$^1$H NMR shows that all proton signals shifted about 0.2 ppm to downfield, compared to that of N-(2-hydroxyethyl)-iminodiacetic acid sodium salt. The ethylene group of $NCH_2COOH$ exhibits a very broad peak at 3.32 ppm, due to the formation of complex. $^1$H NMR ($D_2O$, 300 Hz) 3.71 (t, 2H, J=6 Hz, $OCH_2$), 3.32 (s, broad, 4H, $NCH_2COO$), 2.78 (t, 2H, J=6 Hz, $NCH_2C$), $^{13}$C NMR ($D_2O$, 75 Hz) 178.1, 59.6, 57.4, 57.2. Mass analysis suggests that $Zn^{2+}$ complex contain N-(2-hydroxyethyl)-iminodiacetic acid at m/z 200.1 ($M+Na^+$).

Example 3

Preparation of 6-hydroxy-2,5,7,8-tetramethyl-chroman-2-carboxylic acid 2-dimethylaminoethyl ester

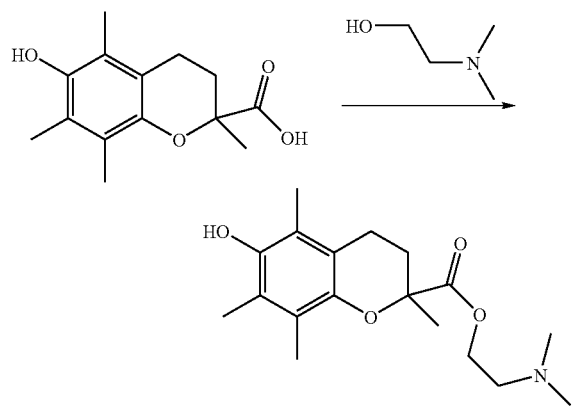

To a stirred solution of 6-hydroxy-2,5,7,8-tetramethyl-chroman-2-carboxylic acid (2.6 g, 10 mmol) in 80 mL of $CH_2Cl_2$ was added dicyclohexylcarbodiimide (2.2 g, 10 mmol). After stirring for 5 min, dimethylaminoethanol (0.93 g, 10 mmol) dissolved in 10 mL of $CH_2Cl_2$ was added to the mixture to form a cloudy suspension. The solution was stirred at room temperature overnight, and the resulting white suspension was filtered to give a clear solution. The solution was washed three times with water, and the organic layer was collected and dried over anhydrous sodium sulfate. The drying agent was removed by filtration and the filtrate was concentrated by rotary evaporation, yielding a viscous, yellowish oil. The residue obtained was loaded to a silica gel column with a mixed solvent of EtOAc and hexane (1:1, v/v). The column was eluted with EtOAc/hexane (1:1, v/v) to remove the less polar impurity. Subsequently, a mixed solvent of $CH_2Cl_2$/MeOH/$NH_4OH$ (90:10:0.5, v/v/v) was used to elute the desired product from the column. 1.2 g of 6-Hydroxy-2,5,7,8-tetramethyl-chroman-2-carboxylic acid 2-dimethylaminoethyl ester were obtained as a viscous yellowish oil, which solidified upon standing at room temperature. MS: m/z=322.2 (M+H$^+$). $^1$H NMR (CDCl$_3$, 300 Hz) 4.19 (t, J=5.8 Hz, 2H), 2.52-1.80 (m, 4H), 2.48 (t, 2H), 2.20 (s, 6H), 2.18 (s, 3H), 2.16 (s, 3H), 2.06 (s, 3H), 1.61 (s, 3H). $^{13}$C NMR (CDCl$_3$, 75 Hz) 173.9, 145.6, 145.4, 122.5, 121.6, 118.8, 116.9, 77.0, 63.3, 57.5, 45.7, 30.6, 25.4, 21.0, 12.3, 11.9, 11.3.

Example 4

Preparation of [(2-Acetoxy-ethyl)-ethoxycarbonylmethyl-amino]-acetic acid ethyl ester

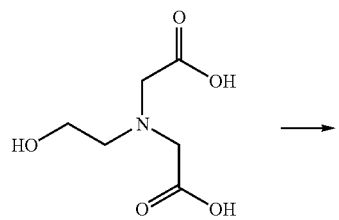

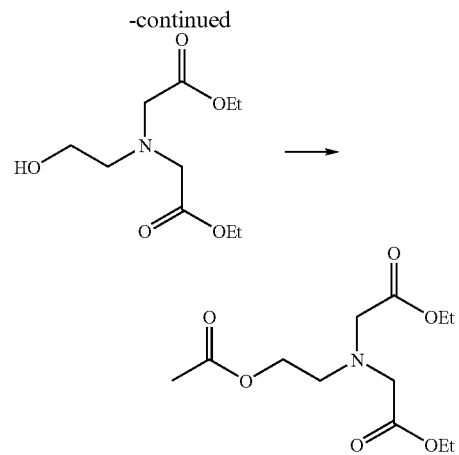

To N-(2-hydroxyethyl)iminodiacetic acid (2.0 g, 11.3 mmol) in 250 mL EtOH was added concentrated HCl (1 mL, 12 mmol). The mixture was stirred for 24 h at rt and concentrated. The residue was partitioned in diethyl ether (150 mL) and NaHCO$_3$ (100 mL, 10% wt). After layer separation, the organic phase was washed with aqueous NaHCO$_3$ (2×50 mL) and dried over Na$_2$SO$_4$ and concentrated and dried under high vacuum. To this crude product in dichloromethane (70 mL) and triethylamine (2.5 g, 24.7 mmol) and was added acetyl chloride (1.57 g, 20 mmol) dropwise. The mixture was stirred at rt for 2 h and diluted with ether (120 mL), washed with 1% NaHCO$_3$ (3×70 mL) and dried over Na$_2$SO$_4$. The solvent was removed under reduced pressure and the residue was chromatographed (Et$_2$O/hexane) to afford a clear oil (1.4 g). $^1$H-NMR (CD3OD, 300 MHz) δ (ppm): 4.17-4.09 (m, 6H), 3.57 (s, 4H), 3.00 (t, J=5.7 Hz, 2H), 2.03 (s, 3H), 1.23 (t, J=7.1 Hz, 6H); $^{13}$C-NMR δ (ppm) 171.1, 170.9, 62.9, 60.5, 55.6, 52.7, 20.9, 14.2; (ESI) m/z: 276 (M+H$^+$, 100).

Example 5

Preparation of [tert-Butoxycarbonylmethyl-(2-hydroxy-ethyl)-amino]-acetic acid tert-butyl ester

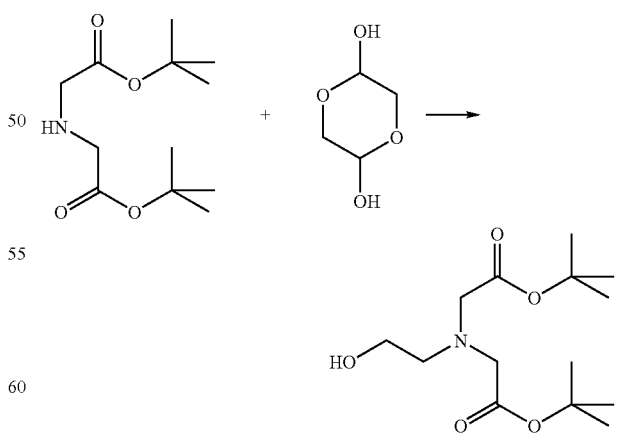

To di-tert-butyl ester (2.45 g, 10 mmol) and alpha-hydroxy acetaldehyde dimer (600 mg, 5 mmol) in 80 mL of CH$_3$CN with stirring was added NaCNBH$_3$ (1.26 g, 20 mmol) in small portions. The reaction was stirred for 10 min followed by the addition of AcOH (600 mg, 10 mmol). The mixture was stirred for another 1.5 h and concentrated under reduced pressure. The residue was taken up in ether (150 mL) and washed with concentrated NaHCO$_3$ (1×100 mL) and 2% NaHCO$_3$ (2×100 mL) and dried over Na$_2$SO$_4$ and concentrated. The residue was chromatographed (dichloromethane/methanol) to afford the desired compound as a yellow oil (1.4 g). $^1$H-NMR (CD$_3$OD, 300 MHz) δ (ppm): 3.51 (t, J=5.0 Hz, 2H), 3.42 (s, 4H), 2.87 (t, J=5.0 Hz, 2H), 1.45 (s, 18H); $^{13}$C-NMR δ (ppm) 171.5, 81.5, 59.3, 57.0, 56.6, 28.1. (ESI) m/z: 290 (M+H$^+$, 100).

Example 6

Preparation of (2-Oxo-morpholin-4-yl)-acetic acid ethyl ester

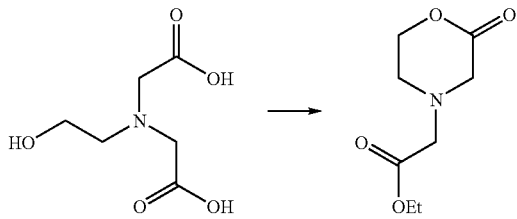

To N-(2-hydroxyethyl)iminodiacetic acid (3.55 g, 20 mmol) in 500 mL EtOH was added concentrated HCl (1.7 mL, 21 mmol). The mixture was stirred for 24 h at rt and concentrated. The residue was partitioned in diethyl ether (200 mL) and NaHCO$_3$ (150 mL, 10% wt). After layer separation, the organic phase was washed with aqueous NaHCO$_3$ (2×100 mL) and dried over Na$_2$SO$_4$ and concentrated and dried under high vacuum. To this crude product in 250 mL of dioxane was added 1.5 mL of HCl and the mixture was heated to reflux for 24 h. After removal of the solvent, the residue was chromatographed (dichloromethane/methanol) to afford a dark yellow oil (1.45 g). $^1$H-NMR (CD$_3$OD, 300 MHz) δ (ppm): 4.40 4.37 (m, 2H), 4.18-4.11 (m, 2H), 3.60 (s, 2H), 3.29 (s, 2H), 2.89-2.86 (m, 2H), 1.25-1.20 (m, 3H); $^{13}$C-NMR δ (ppm) 169.4, 167.0, 68.6, 60.9, 57.0, 54.5, 48.2, 14.2. (ESI) m/z: 188 (M+H$^+$, 100).

Example 7

High Glutamate-Induced Oxidative Stress Assay

This protocol describes the procedure used to induce high glutamate-induced oxidative stress (HGOS) in a dopaminergic neuronal cell line. Using this assay the potency and efficacy of test articles against HGOS neuronal cell injury and cell death can be established in a high throughput manner.

Procedures and Materials

Materials
  Dopaminergic neuronal cell lines
  DMEM-No Glucose (Life Technologies Cat # 11966-025)
  L-glutamine (Life Technologies Cat # 25030-081)
  L-glutamic acid, monosodium salt (Sigma Cat # G5889)
  D-glucose (Sigma Cat # G-6151)
  10×HBSS buffer (pH 7.4) (950 ml Pyrogen-free water, 2.44 g/L MgCl2.6H20, 3.73 g/L KCl, 59.58 g/L Hepes, 58.44 g/L NaCl, 1.36 g/L KH2PO4, 1.91 g/L CaCl2.2H2O and pH to 4.5 with HCl)
  Cell Tracker Green fluorescent dye (Molecular Probes, Cat # 2925). Prepare a 5 μM solution in pre-warmed HBSS just prior to use.
  Sterile 96-well plates precoated with poly-D-lysine (Corning Catalog # 3665)
  96-well deep well mother plate, DyNA Block 1000 (VWR-Catalog # 40002-008)

Neuronal Cells

The cells were seeded into 96-well plates at a density of 2000 per well and left to grow for 72 hours in a 33° C. incubator with 5% CO$_2$ in air atmosphere. The passage number of the cells for each assay experiment were no later than p11 in order to minimize experimental variation.

Compound Preparation in Deep-Well Mother Plates

VWRBrand DyNA Block 1000, deep well mother plates (VWRCat. # 40002-008) were used for the preparation of the test compounds.

All compounds were dissolved in DMEM-No Glu containing 1 mM glucose, 30 mM glutamate and 1×Pen/Strep. DMEM-No Glu with 1 mM glucose and 1×P/S was used as the negative control, DMEM-No Glucose with 1 mM glucose, 100 M glutamate was used as a positive control and 100 μM Glutathione was added to the positive control as a standard. All of the procedures for this involving the making and dilution of compounds were performed using aseptic conditions and with minimal light.

Cell Preparation

The plates were removed from the incubator and examined under the microscope for morphological appearance and density. Using an aseptic technique and an 8-channel aspirator the media was carefully removed from the cells and replaced with 200 μl of 1×HBSS. This was done as quickly as possible to prevent the cells drying out. The plates were then placed in the humidified 37° C. incubators of the Biomek 2000 Side Loader. Four plates were washed at a time so as to minimize the time that the cells were sitting in 1×HBSS prior to addition of the compound test solution.

Experimental Setup

The Beckman Biomek workstations were used to load the compounds and controls from the mother plates onto the cell plates that were prewashed with HBSS under sterile conditions. The plates were incubated in the upper HTS incubator at 37° C. in 5% CO$_2$ for exactly 16 hrs. The following day, using the Beckman Biomek workstations, the plates were removed from the incubator. Using Cell Tracker Addition, the compounds were removed from the plates, washed once with 200 μM of pre-warmed 1×HBSS and then 100 μL of 5 μM Cell Tracker Green was added to each well. The plates were incubated at 37° C. for 30 min to allow the dye to enter the cell and be cleaved by the esterases. After washing the cells twice with prewarmed 1×HBSS, the plates were read with the 485 excitation; 538 emission filter pair on a Fluoroskan.

Compounds of the present invention were considered to be active when they exhibited protection against HGOS cell injury and cell death at an EC$_{50}$ in a range of less than 10 μM.

Example 8

Clinical Evaluation for Dark Circles

Women subjects with mild to moderate dark circles under their edges are recruited for the study. Both an expert grader and the panelists evaluate the severity of the dark circles under their eyes prior to application of test products. The composition containing compounds of the invention is topically applied to the skin area around one eye and a composition not containing the inventive compounds around the opposite eye. Treatment assignments are randomized across the panel, and neither the panelist nor the grader, have knowledge of the treatment code. One hour after product application, both the grader and panelist can separately evaluate the appearance of the dark circles under the eyes.

Example 9

Clinical Evaluation for Puffiness

A set of women subjects with puffiness under their eyes are recruited, and a composition containing the inventive compound is applied under one eye, and a composition with no inventive compound is applied under the other eye. The panelists use the product for 4 weeks, returning at week 2 for another dermatologist evaluation. After 2 and 4 weeks of product use, both the panelists and the dermatologist can evaluate the improvement in the puffiness of the eyes compared with the baseline observations.

Example 10

Clinical Evaluation for Ageing Signs

Expert graders that have been trained to visual and tactile evaluations assess the different ageing signs of the face by grading on semi-structured scale. Each subject is characterized by a quantitative profile of its ageing signs and two expert graders evaluate each parameter at each time point.

Mean values and standard deviation is calculated, as well as variations of the parameter relative to before application (expressed in percentage). Paire Student's t test is used to determine the significance of the results.

Example 11

Measurements with Reviscometer® RVM 600

The Reviscometer®RVM 600, developed by Courage Khazaka Electronic GmbH, is an instrument used to measure skin firmness. This device consists of a probe that places two needle sensors on the skin. One sensor transmits an acoustical shockwave while the other receives the wave after it has propagated along the surface of the skin.

One determination is performed on each area and at each time point on the neck or arm. The place of the probe is marked with an ink and a mask of the neck with ears, the spots and the most important wrinkles, is done to reposition the probe exactly at the same place after one week of application and 45 minutes after the last application.

Results are expressed for all the subjects at each time point.

The area under curve is considered and standard deviations are calculated. Paired Student's test is used to determine the significance of the results.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto. All patents and publications cited above are hereby incorporated by reference.

We claim:

1. A for reducing the appearance of skin wrinkles, sagging in the eye area or jowls, frown lines, expression lines, striae, stretch marks, loss of skin elasticity, loss of skin tightness, loss of skin firmness, loss of skin recoil from deformation, loss of collagen and elastic fibers, comprising topically applying to affected skin areas a composition comprising an effective amount of N-(2-hydroxyethyl)-iminodiacetic acid or acceptable salts thereof.

2. The method of claim 1, comprising administering a composition comprising the effective amount of N-(2-hydroxyethyl)-iminodiacetic acid in admixture with at least one cosmetically acceptable excipient.

3. The method of claim 1, wherein the treatment is for improving the appearance of loss of skin elasticity, skin tightness or skin firmness.

4. The method of claim 1, comprising administering a topical composition comprising the effective amount of N-(2-hydroxyethyl)-iminodiacetic acid with at least one additional benefit agent selected from sunscreens, retinoids, antioxidants; hydroxyacids; fatty acids; acceptable non-toxic organic salts of zinc, copper or magnesium, optionally derived from naturally occurring amino acids or from hydroxyalkyl acids; botanical extracts; salicylic acid; benzoyl peroxide; antibiotics; antiandrogens; anti-inflammatory agents; ascorbic acid; vitamins B, tocopherols or tocotrienols; corticosteroids, or mixtures thereof.

* * * * *